(12) United States Patent
Tanaka et al.

(10) Patent No.: US 6,534,050 B1
(45) Date of Patent: Mar. 18, 2003

(54) 2-METHYL-3-BUTENYL-1-PYROPHOSPHORIC ACID SALTS AND AGENTS FOR TREATING LYMPHOCYTES

(75) Inventors: Yoshimasa Tanaka, Tokyo (JP); Takehiko Uchiyama, Tokyo (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/889,782

(22) PCT Filed: Jan. 21, 2000

(86) PCT No.: PCT/JP00/00273
§ 371 (c)(1),
(2), (4) Date: Jul. 20, 2001

(87) PCT Pub. No.: WO00/43403
PCT Pub. Date: Jul. 27, 2000

(30) Foreign Application Priority Data

Jan. 21, 1999 (JP) ............................................. 11-013343

(51) Int. Cl.[7] .............................. A61K 47/06; C07F 9/09
(52) U.S. Cl. ........................ 424/85.2; 514/47; 514/814; 514/885; 530/351; 558/70; 568/8
(58) Field of Search ........................ 424/85.2; 530/351; 514/47, 814, 885; 558/70; 568/8

(56) References Cited

U.S. PATENT DOCUMENTS 5,639,653 A * 6/1997 Bloom et al.

OTHER PUBLICATIONS

Koyama, et al, 'Phytochemistry, vol. 27 No. 7, pp. 2005–2009 (1988).

Pozzi, et al, Angew. Chem., Int. Ed. Engl., vol. 35 No. 2, pp. 177–180 (1996).

\* cited by examiner

*Primary Examiner*—Christina Chan
*Assistant Examiner*—Phuong Huynh
(74) *Attorney, Agent, or Firm*—Birch, Stewart, Kolasch & Birch, LLP (57) ABSTRACT

A pharmaceutically acceptable salt of 2-methyl-3-butenyl-1-pyrophosphoric acid; an agent for treating lymphocytes which comprises at least one of 2-methyl-3-butenyl-1-pyrophosphoric acid, a pharmaceutically acceptable salt thereof, and a hydrate thereof; Vγ2Vδ2 type T cells treated by the same; and a medicine containing the same specifically stimulate and proliferate the human Vγ2Vδ2 type T cells, and also induce and enhance an antitumor activity thereof.

7 Claims, 9 Drawing Sheets

2-METHYL-3-BUTENYL-1-PYROPHOSPHORIC ACID SALTS AND AGENTS FOR TREATING LYMPHOCYTES

This application is the national phase under 35 U.S.C. § 371 of PCT International Application No. PCT/JP00/00273 which has an International filing date of Jan. 21, 2000, which designated the United States of America.

TECHNICAL FIELD

The present invention relates to a novel salt of an organic pyrophosphoric acid compound. It also relates to an agent for treating lymphocytes containing the organic pyrophosphoric acid compound or the salt thereof which effectively induces and potentiates an antitumor effect, Vγ2Vδ2 type T cells treated by the agent for treating lymphocytes and to a medicine containing the same.

BACKGROUND ART

As a method for inducing and enhancing an antitumor effect in human lymphocytes, it has been known LAK therapy using interleukin-2. That is, it has been known that by having about 800 U/ml of interleukin-2 to act on the lymphocytes, cell groups induced thereby with an antitumor activity can be used as an antitumor effecter. However, in this method, there are serious side effects, for example, destruction of the self cells such as endovascular cells due to non-specific cytotoxic property possessed by LAK cells and the like or induction of autoimmunity due to non-specific activation of T cells by interleukin-2, thereby making it difficult to apply this methods to an actual clinical field.

As compounds which specifically activate Vγ2Vδ2 type T cells, there have been known mycobacteria-derived isopentenyl pyrophosphoric acid and mono ethyl phosphoric acid obtained by an organic synthesis. In those methods, however, the concentrations of those compounds are required to be several hundreds of $\mu$M to several mM in order to activate Vγ2Vδ2 type T cells. Such high concentrations of the compounds may have a toxic effect on the cells, therefore, it was difficult to use those compounds to induce and enhance an antitumor effect of the lymphocytes in a large scale. In any case, it has not yet been known a synthetic compound which can act on the Vγ2Vδ2 type T cells in a concentration of several hundreds of nM to several hundreds of $\mu$M, and specifically proliferate those cell groups.

The present invention has been aimed to solve the above-mentioned problems of the prior art. An object of the present invention is to provide a novel compound that can specifically stimulate and proliferate the human Vγ2Vδ2 type T cells, an agent for treating lymphocytes that induces and/or potentiates an antitumor effect of the human Vγ2Vδ2 type T cells, Vγ2Vδ2 type T cells treated by the same, and a medicine which comprises the same.

SUMMARY OF THE INVENTION

The present inventors have made extensive and intensive studies in search for a compound that can specifically stimulate and proliferate the human Vγ2Vδ2 type T cells thereby inducing and enhancing the antitumor effect thereof. As a result, they have found a pharmaceutically acceptable salt of 2-methyl-3-butenyl-1-pyrophosphoric acid, especially a sodium salt thereof as a novel organic pyrophosphoric acid compound. That is, they have found that, when lymphocytes in human blood such as peripheral blood or the lymph are treated by such an organic pyrophosphoric acid compound, Vγ2Vδ2 type T cells are specifically stimulated and proliferated whereby the antitumor effect thereof are induced and potentiated, and thus, the present invention has been completed.

Accordingly, the present invention relates to a pharmaceutically acceptable salt of 2-methyl-3-butenyl-1-pyrophosphoric acid which is a novel organic pyrophosphoric acid compound, especially a sodium salt thereof and to an agent for treating lymphocytes which comprises at least one selected from the group consisting of 2-methyl-3-butenyl-1-pyrophosphoric acid, a pharmaceutically acceptable salt thereof, especially a sodium salt thereof, and a hydrate thereof. Further, the present invention relates to Vγ2Vδ2 type T cells treated by the agent for treating lymphocytes, and a medicine which comprises the same.

BEST MODE FOR CARRYING OUT THE INVENTION

The novel pyrophosphoric acid compound of the present invention is a pharmaceutically acceptable salt of 2-methyl-3-butenyl-1-pyrophosphoric acid, and sodium salt is a representative. The sodium salt is represented by the formula (I):

(wherein each of X independently represents a hydrogen atom or a sodium atom, at least one of which is a sodium atom). It is preferable that 2 of X are sodium atoms due to the compatibility to in vivo cells. Further, it can contain water of crystallization. As a pharmaceutically acceptable salt, there may be mentioned a potassium salt, an ammonium salt, a triethyl ammonium salt and an amino acid salt such as lysine salt in addition to the above-described sodium salt.

2-Methyl-3-butenyl-1-pyrophosphoric acid sodium salt of the present invention can be synthesized, for example, in a method described as follows. That is, 2-methyl-3-butenyl-1-ol is reacted in a solvent such as acetonitrile with bis (triethyl ammonium)phosphoric acid using trichloroacetonitrile as a catalyst. The obtained reaction product is separated with diethyl ether and an aqueous ammonia solution, then, the product extracted in the diethyl ether layer is applied to an anion exchange column chromatography, followed by elution from triethyl ammonium bicarbonate buffer by a concentration radient method, to obtain 2-methyl-3-butenyl-1-pyrophosphoric acid. Subsequently, it is treated with a Na type cation exchange resin to obtain a sodium salt. Other pharmaceutically acceptable salts can be synthesized according to the above method.

The thus obtained sodium salt of 2-methyl-3-butenyl-1-pyrophosphoric acid is white powder with deliquenscence, which becomes a white viscous substance when it contains water. When it is dissolved in a neutral aqueous solution, for example, at pH 6 to 7, it can be stably preserved more than one week at room temperature, and more than one year at −20° C. However, in an acidic range of pH 4 or less, dissociation of inorganic pyrophosphoric acid is observed within a few minutes.

2-Methyl-3-butenyl-1-pyrophosphoric acid, a pharmaceutically acceptable salt thereof, especially a sodium salt thereof and a hydrate thereof specifically stimulate and proliferate the human Vγ2Vδ2 type T cells existing in the human blood such as the peripheral blood or the human lymph, and at the same time, they promote induction and enhancement of antitumor activity of those cells. As the pharmaceutically acceptable salt, the above-mentioned salts are exemplified.

Accordingly, when the human blood or lymph is treated with an agent for treating lymphocytes of the present invention containing at least one kind of the above mentioned organic pyrophosphoric acid derivatives, it specifically stimulates and proliferates the human Vγ2Vδ2 type T cells, and at the same time, it can induce and enhance the antitumor activity thereof. In this case, an analysis using the human Vγ2Vδ2 type T cell clones shows that 2-methyl-3-butenyl-1-organic pyrophosphoric acid compound, especially the above described novel sodium salt can stimulate the cells even in a very small amount such as several hundreds nM to several tens μM, and proliferate the human Vγ2Vδ2 type T cells in the presence of a very small amount of several hundreds μM, thereby inducing and enhancing the antitumor activity thereof.

As an organic pyrophosphoric acid compound to be contained as an active component in the agent for treating lymphocytes of the present invention, it is exemplified by the above-mentioned 2-methyl-3-butenyl-1-pyrophosphoric acid, a pharmaceutically acceptable salt thereof and a hydrate thereof. Among those, a sodium salt is preferable due to a good compatibility to in vivo cells, and a sodium salt wherein 2 of X are sodium atoms in the above-mentioned formula (I) is especially preferable. Those salts can be used in combination without a need for isolation, in a proper pH range to meet the requirements, preferably in a range of pH 6 to 7

When the agent for treating lymphocytes containing the above-mentioned organic pyrophosphoric acid compound is acted on the human blood, especially on the peripheral blood, if interleukin-2 is added as a cofactor in a concentration of 1 to 20 U/ml, specific proliferation of the Vγ2Vδ2 type T cells becomes outstanding. As long as the concentration of the interleukin-2 is limited under 20 U/ml, non-specific activation of the lymphocytes would not occur different from the case of the LAK cells. Further, it is possible to use other cofactor such as interleukin-15. The human Vγ2Vδ2 type T cells have a kind of natural killer activity. The present invention is completely different from conventional induction methods of the antitumor activity in that it can proliferate those cell groups antigen-specifically.

That is, in the LAK therapy and the TIL therapy, the cell proliferation factor such as intrerleukin-2 is added excessively thereby forcibly activating naive cell groups in the peripheral blood. Therefore, it is accompanied by side effects such as attacking the self cells. On the contrary, the above-mentioned organic pyrophosphoric acid compound is naturally to be used to proliferate the population of the Vγ2Vδ2 type T cells having natural killer activity, therefore, it is not excessively and forcibly enhancing the antitumor activity by using an excess amount of the antigen. The concentration of 20 μM of the above-mentioned organic pyrophosphoric acid type antigen corresponds to the activity of 10 to 50 U, and is appropriate as a concentration. Therefore, proliferation and activation of the human Vγ2Vδ2 type T cells and induction and enhancement of the antitumor activity thereof by the present invention is immunochemically appropriate causing no destruction of the self cells. From the above, the agent for treating lymphocyte of the present invention is a more advantageous agent for inducing and enhancing the antitumor activity due to its higher specificity and less side effects in comparison to the LAK therapy and the TIL therapy.

In addition, the use of the agent for treating lymphocytes of the present invention is advantageous in that it is possible to freeze the treated cells. That is, the blood containing lymphocytes and/or the lymph are collected at the suitable point and preserved by freezing then as necessity arises, the lymphocytes are activated by the above-mentioned organic pyrophosphoric acid compound. By proliferating the Vγ2Vδ2 type T cells as mentioned above, and by inducing and enhancing the antitumor activity thereof, it is possible to decrease a burden for donors of peripheral blood lymphocytes.

Further, since the human Vγ2Vδ2 type T cells have natural killer activity, even if it is preserved by freezing after the antitumor activity is induced and potentiated, it can exhibit the antitumor activity immediately after it thaws. This makes it possible to use the cell at any time. On the contrary, the LAK therapy and the TIL therapy require fresh cells all the time, and every time the antitumor activity is induced and potentiated, the lymphocytes should be collected and the proliferation factor should be added. From the above-mentioned facts, the therapy using the agent for treating lymphocytes of the present invention is clearly more advantageous than the LAK therapy and the TIL therapy.

Therefore, the present invention enables the wide range of antitumor therapy in the practical medical field by using a medicine which comprises the human Vγ2Vδ2 type T cells whose antitumor activity is induced and potentiated.

The Vγ2Vδ2 type T cells which are treated and proliferated with the agent for treating lymphocytes of the present invention, and whose antitumor activity is induced and potentiated can exhibit the antitumor activity by returning those T cells themselves into the human patient as the peripheral blood. The administration method includes a local injection, intravenous injection, endermic absorption and the like.

The thus treated Vγ2Vδ2 type T cells are free from MHC limitation and it is possible to administer them to the other person.

Therefore, the present invention includes the Vγ2Vδ2 type T cells which are treated with the agent for treating lymphocytes of the present invention and a medicine containing the same.

When the compound of the present invention or the agent for treating lymphocytes containing the same is administered as a medicine, it can be prepared by a general preparation technique, and it can be used as a solid or liquid preparation form such as a tablet, a capsule, powders, granules, a suppository, cream, an ointment, an aqueous solution, an emulsion, oil or a suspension and the like.

Further, in that case, except for preparations whose pH is 4 or less, generally used additives in the preparation can be used as necessity arises, such as an excipient, a disintegrator, a lubricant, a binder, a preservative, a stabilizer, an osmotic pressure adjuster, a substrate and the like.

The examples of the above-mentioned additives include glucose, lactose, starch, carboxymethyl cellulose, magnesium stearate, talc, liquid paraffin, polyvinyl alcohol, vegetable oil, polyalkylene glycol, and the like. It can also contain a medical component in addition to these.

EXAMPLES

The present invention will be explained in more detail referring to Examples and Test examples hereinbelow. These examples, however, are not construed to limit the scope of the present invention.

In Test examples, treatment of the peripheral blood by 2-methyl-3-butenyl-1-pyrophosphoric acid or by a salt thereof was conducted as follows unless otherwise specified. Lymphocytes contained in the peripheral blood derived from healthy volunteer were treated so that the final concentration of the pyrophosphoric acid compound was 20 μM, and cultured in a Yssel's medium under conditions of temperature at 37° C. and a carbon dioxide concentration of 5%. After 2, 4, 6, 8 and 10 days, interleukin-2 was added in an amount of 10 U/ml, respectively, as a cofactor. After 12 days, the cells were collected.

EXAMPLE

Synthesis of Sodium Salt of 2-Methyl-3-butenyl-1-pyrophosphoric Acid

To 1 mol of 2-methyl-3-butenyl-1-ol was added 1 mol of trichloroacetonitrile as a catalyst, and while stirring at a temperature of 25° C., 4 mol of bis (triethyl ammonium) phosphoric acid dissolved in 20 ml of acetonitrile was added dropwise over 4 hours and reacted while stirring for another 2 hours. To the reaction product was added 100 ml of diethyl ether and the mixture was transferred to a separation funnel. 100 ml of 0.88% aqueous ammonia was added thereto and shaken, and the obtained organic pyrophosphoric acid was extracted in an organic layer. After diethyl ether was evaporated from the organic layer under a reduced pressure, the resultant liquid was subjected to Q Sepharose HP anion exchange column chromatography having a diameter of 2.5 cm and a length of 8 cm, then washed with water.

Figure 1:
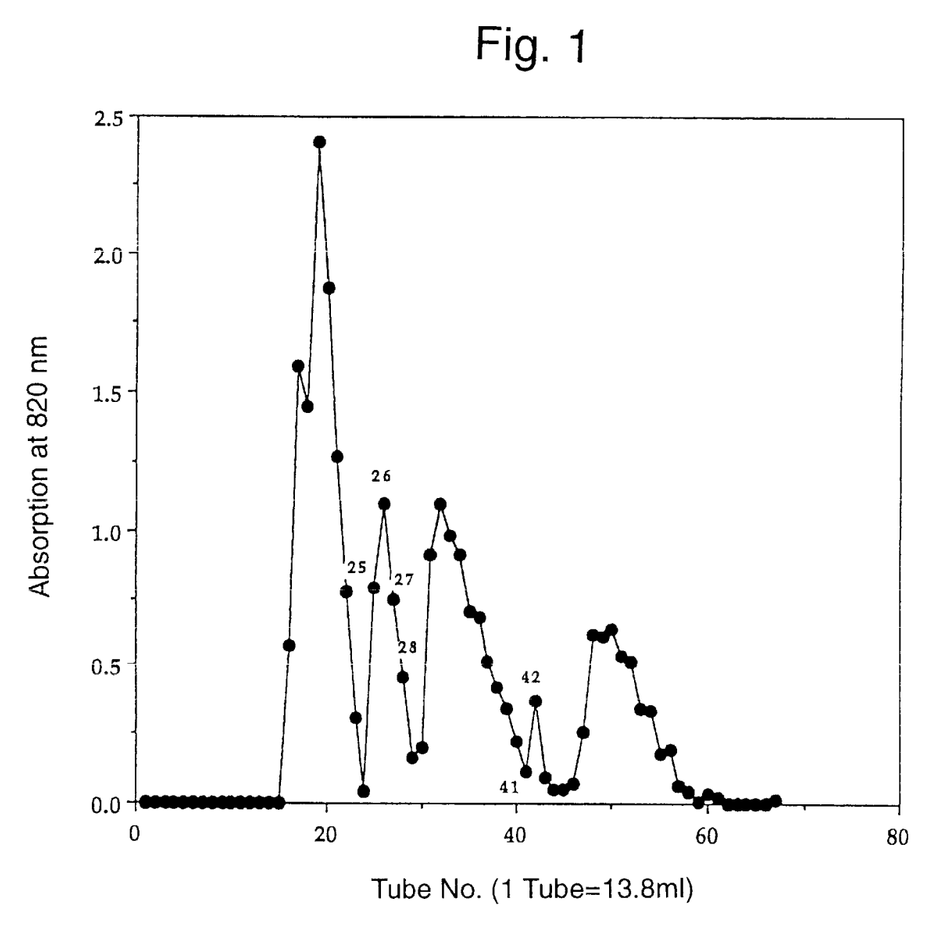
FIG. 1 is a chromatogram showing an elution curve of the sodium salt of 2-methyl-3-butenyl-1-pyrophosphoric acid synthesized in Example by Q sepharose HP column chromatography using 820 nm absorption as a parameter.

Subsequently, using a triethyl ammonium bicarbonate buffer, the organic pyrophosphoric acid compound was eluted by a concentration gradient method from 0 to 500 mM. An elution curve of the column chromatography with absorption at 820 nm as a parameter is shown in FIG. 1. Here, a fraction eluted in an area of approximately 150 to 200 mM was 2-methyl-3-butenyl-1-pyrophosphoric acid. After freeze-dried this fraction, it was dissolved in 2 ml of water and the solution was treated by Na type Dowex 50 W cation exchange resin (Trade name of Dow Chemical Co.) to obtain a sodium salt of 2-methyl-3-butenyl-1-pyrophosphoric acid containing a little amount of water as a white viscous substance. It was dried to obtain a sodium salt of 2-methyl-3-butenyl-1-pyrophosphoric acid as white powder.

TEST EXAMPLE 1

Figure 2:
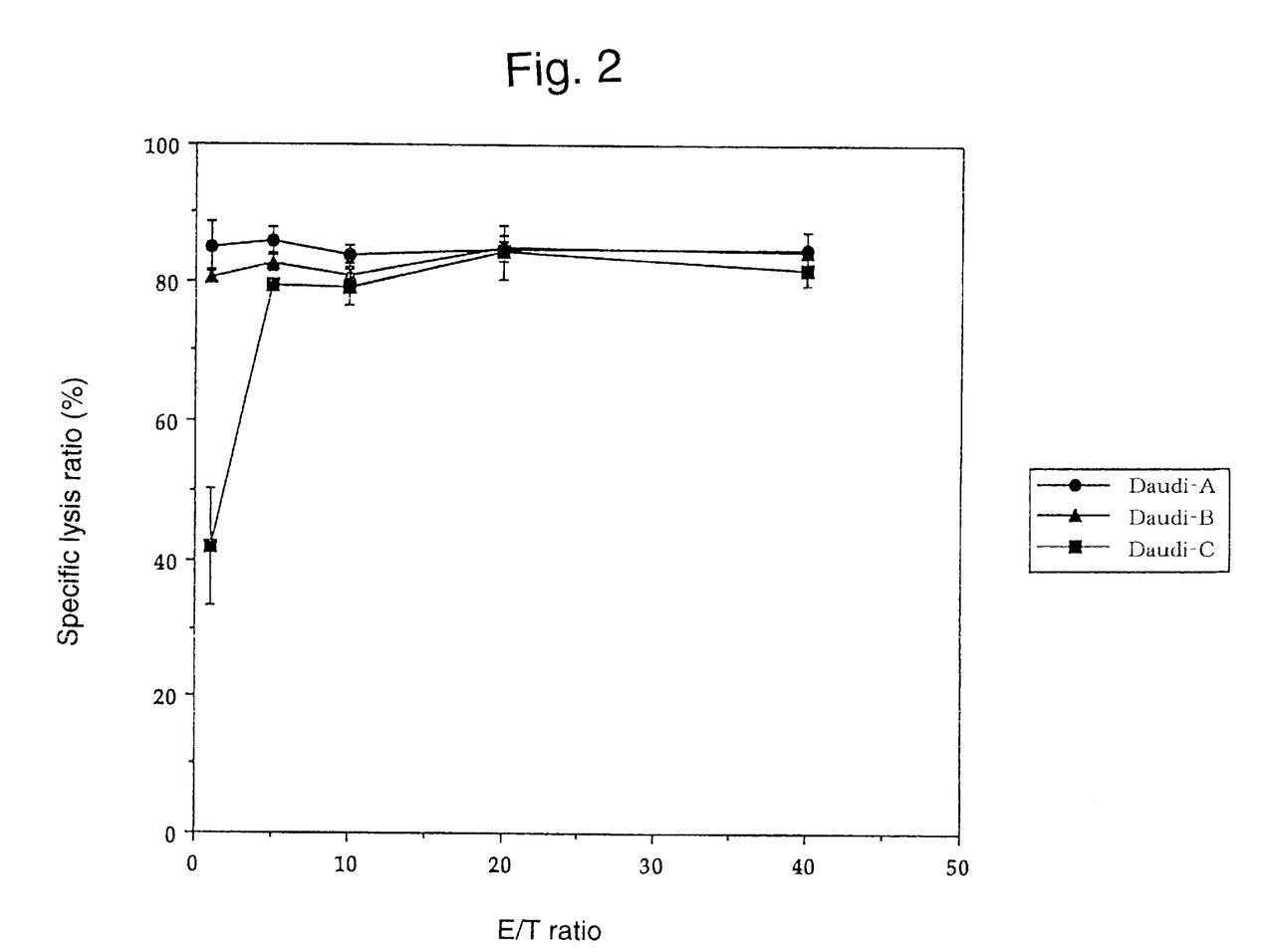
FIG. 2 is a graph showing a relation of a specific lysis ratio relative to an E/T ratio when Vγ2Vδ2 type T cells treated in Test 1 acted on Daudi cells.

Using the sodium salt of 2-methyl-3-butenyl-1-pyrophosphoric acid obtained in Example, proliferation of the human Vγ2Vδ2 type T cells and induction and enhancement by the treatment of the human peripheral blood derived from healthy volunteers A, B and C were conducted according to the above-mentioned method. The peripheral blood containing the potentiated human Vγ2Vδ2 type T cells were acted on Daudi cells to analyze cytotoxicity. The results are shown in FIG. 2. In FIG. 2, the transverse axis shows an effecter/target ratio (hereinafter refer to as an E/T ratio), that is, a ratio of existing human Vγ2Vδ2 type T cells and Daudi cells. The vertical axis shows a specific lysis ratio.

As is apparent from FIG. 2, in both case of the peripheral blood of A and B, cytotoxicity reached a plateau even when the E/T ratio is 1:1, exhibiting a high cytotoxic effect. In the case of the peripheral blood of C, cytotoxicity reached the same level when the E/T ratio is 5:1.

TEST EXAMPLE 2

Figure 3:
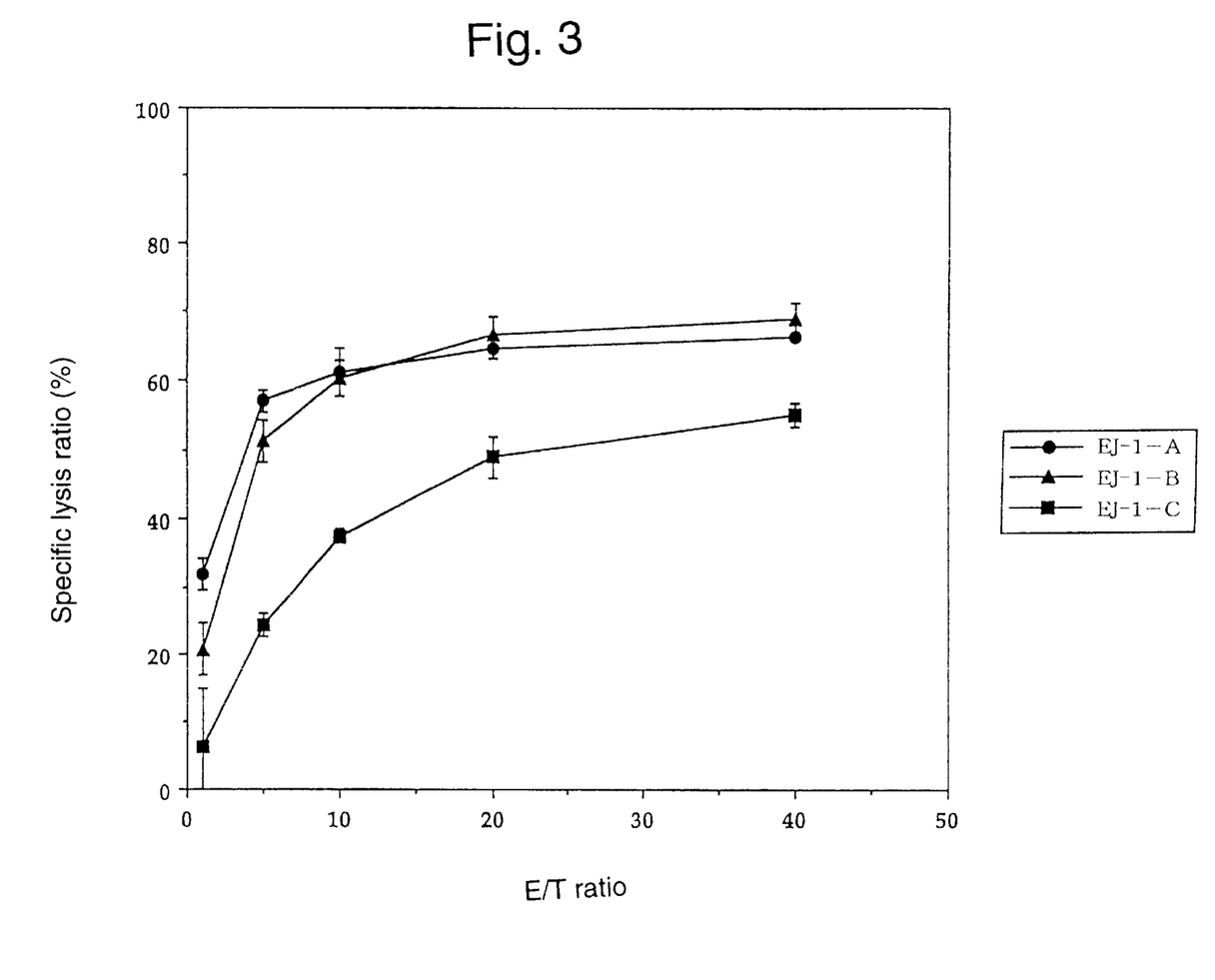
FIG. 3 is a graph showing a relation of a specific lysis ratio relative to an E/T ratio when Vγ2Vδ2 type T cells treated in Test example 2 acted on EJ-1 cells.

Using the sodium salt of 2-methyl-3-butenyl-1-pyrophosphoric acid obtained in Example, proliferation of the human Vγ2Vδ2 type T cells and induction and enhancement by treatment of the human peripheral blood derived from healthy volunteers A, B and C were conducted in the same manner as in Test example 1 according to the above-mentioned method. The peripheral blood containing the potentiated human Vγ2Vδ2 type T cells were acted on EJ-1 cells to analyze cytotoxicity. The results are shown in FIG. 3. In FIG. 3, the transverse axis shows an E/T ratio, and the vertical axis shows a specific lysis ratio.

As is apparent from FIG. 3, in both cases of the peripheral blood of A and B, cytotoxicity reached a plateau when the E/T ratio is 5:1, and in case of the peripheral blood of C, cytotoxicity reached approximately a plateau when the E/T ratio is 10:1.

TEST EXAMPLE 3

Figure 4:
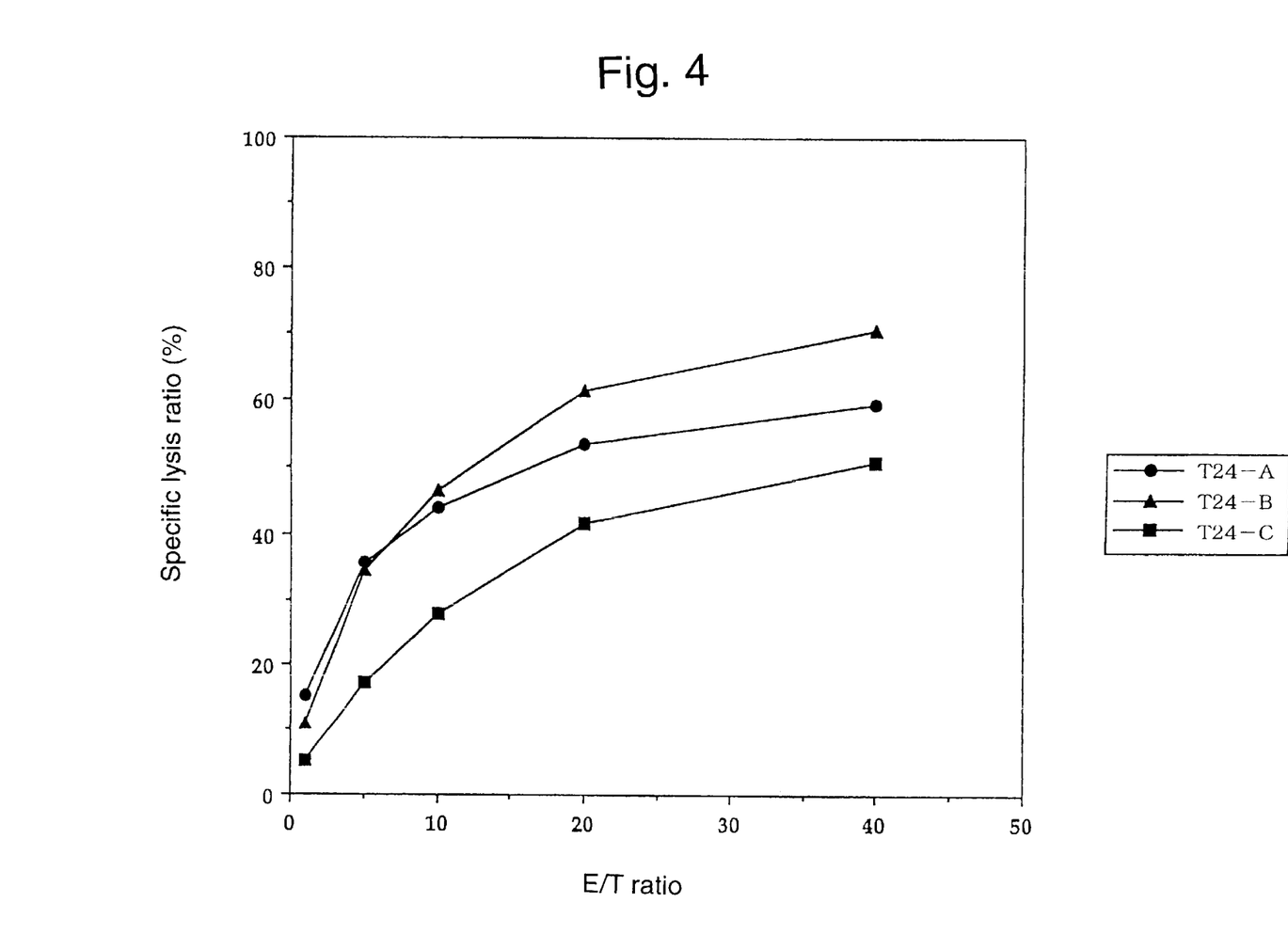
FIG. 4 is a graph showing a relation of a specific lysis ratio relative to an E/T ratio when Vγ2Vδ2 type T cells treated in Test example 3 acted on T24 cells.

Using the sodium salt of 2-methyl-3-butenyl-1-pyrophosphoric acid obtained in Example, proliferation of the human Vγ2Vδ2 type T cells and induction and enhancement by treatment of the human peripheral blood were conducted according to the above-mentioned method. The peripheral blood containing the potentiated human Vγ2Vδ2 type T cells were acted on T24 cells to analyze cytotoxicity. The results are shown in FIG. 4. In FIG. 4, the transverse axis shows an E/T ratio, and the vertical axis shows a specific lysis ratio.

As is apparent from FIG. 4, in all cases of the peripheral bloods of A, B and C, cytotoxicity reached approximately a plateau when the E/T ratio is 20:1.

TEST EXAMPLE 4

Figure 5:
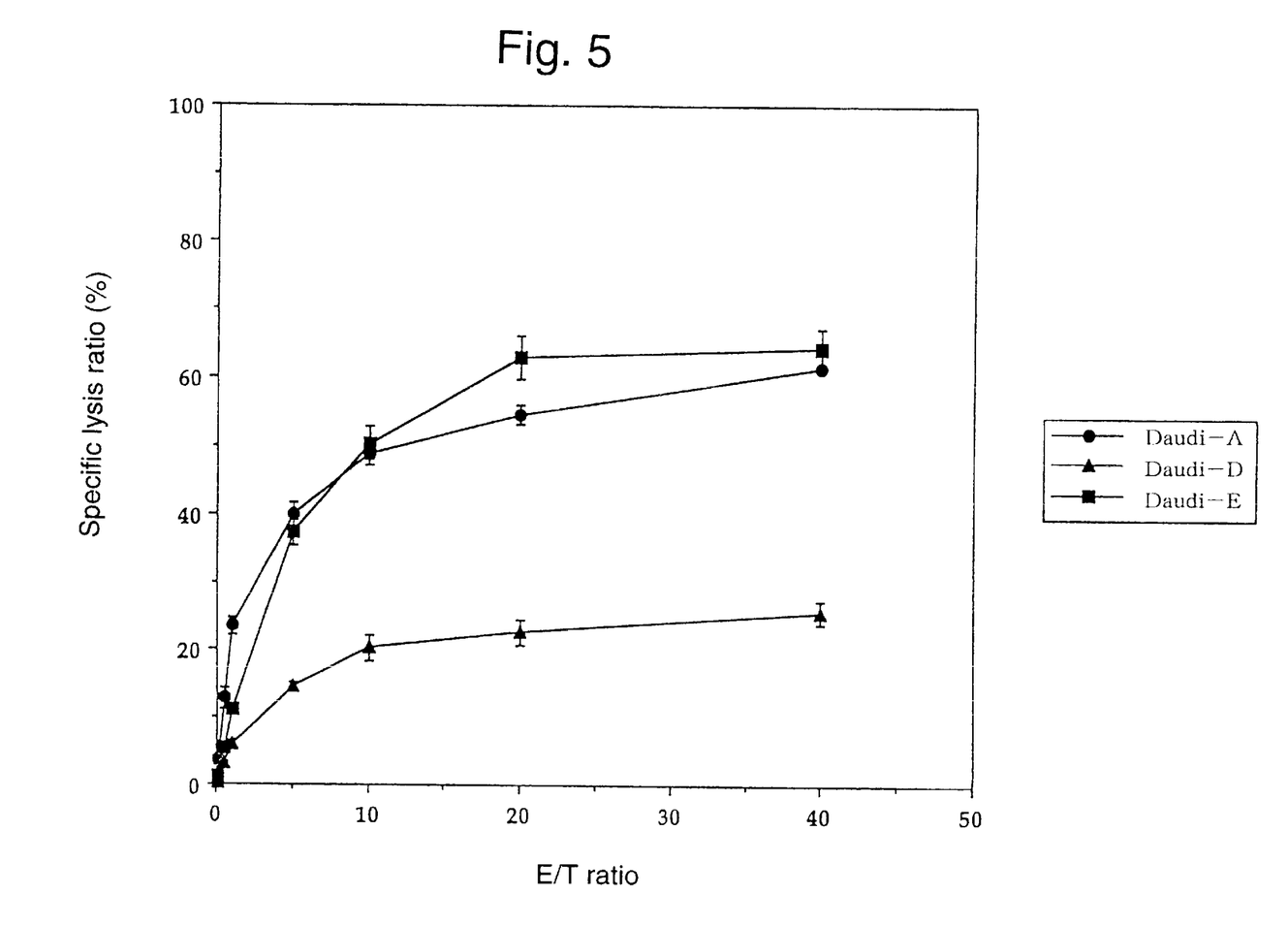
FIG. 5 is a graph showing a relation of a specific lysis ratio relative to an E/T ratio when Vγ2Vδ2 type T cells treated in Test example 4, subsequently frozen for preservation and thawed, acted on Daudi cells.

Using the sodium salt of 2-methyl-3-butenyl-1-pyrophosphoric acid obtained in Example, proliferation of the human Vγ2Vδ2 type T cells and induction and enhancement by treatment of the human peripheral blood were conducted according to the above-mentioned method using the peripheral blood of the volunteer A and other healthy volunteers D and E. Thus obtained treated peripheral blood was preserved by freezing for one year at −20° C. The treated and preserved blood after being thawed were acted on Daudi cells to analyze cytotoxicity. The results are shown in FIG. 5. In FIG. 5, the transverse axis shows an E/T ratio, and the vertical axis shows a specific lysis ratio.

As is shown by FIG. 5, in both cases of the peripheral bloods of A and E, cytotoxicity reached approximately a plateau when the E/T ratio is 20:1, and in a case of the frozen-preserved peripheral blood of D, cytotoxicity reached a plateau when the E/T ratio is 20:1 while there is a difference in degree. As a result, it is evident that the treated lymphocytes maintain sufficient antitumor effect even after they are preserved by freezing.

TEST EXAMPLE 5

Figure 6:
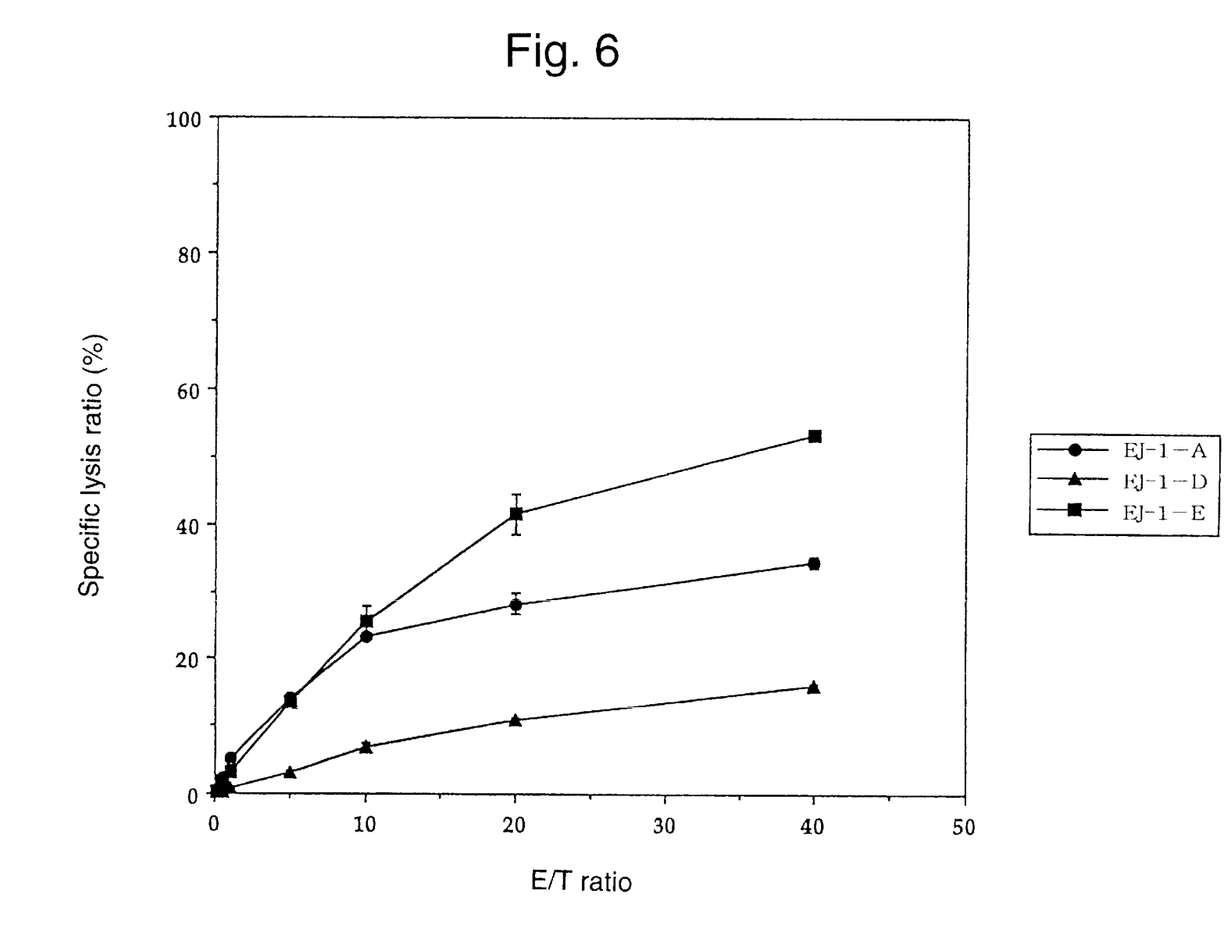
FIG. 6 is a graph showing a relation of a specific lysis ratio relative to an E/T ratio when Vγ2Vδ2 type T cells treated in Test example 5, subsequently frozen for preservation and thawed, acted on EJ-1cells.

Using the sodium salt of 2-methyl-3-butenyl-1-pyrophosphoric acid obtained in Example, proliferation of the human Vγ2Vδ2 type T cells by treatment of the human peripheral blood and induction and enhancement as well as preservation by freezing and thawing were conducted in the same manner as in Test example 4. The treated and preserved blood was acted on the EJ-1 cells to analyze cytotoxicity. The results are shown in FIG. 6. In FIG. 6, the transverse axis shows an E/T ratio, and the vertical axis shows a specific lysis ratio.

As is apparent from FIG. 6, cytotoxicity reached approximately a plateau when the E/T ratio is 20:1 in any case while there is a difference in degree. And it is observed that the antitumor effect was maintained even after the cells are preserved by freezing.

TEST EXAMPLE 6

Figure 7:
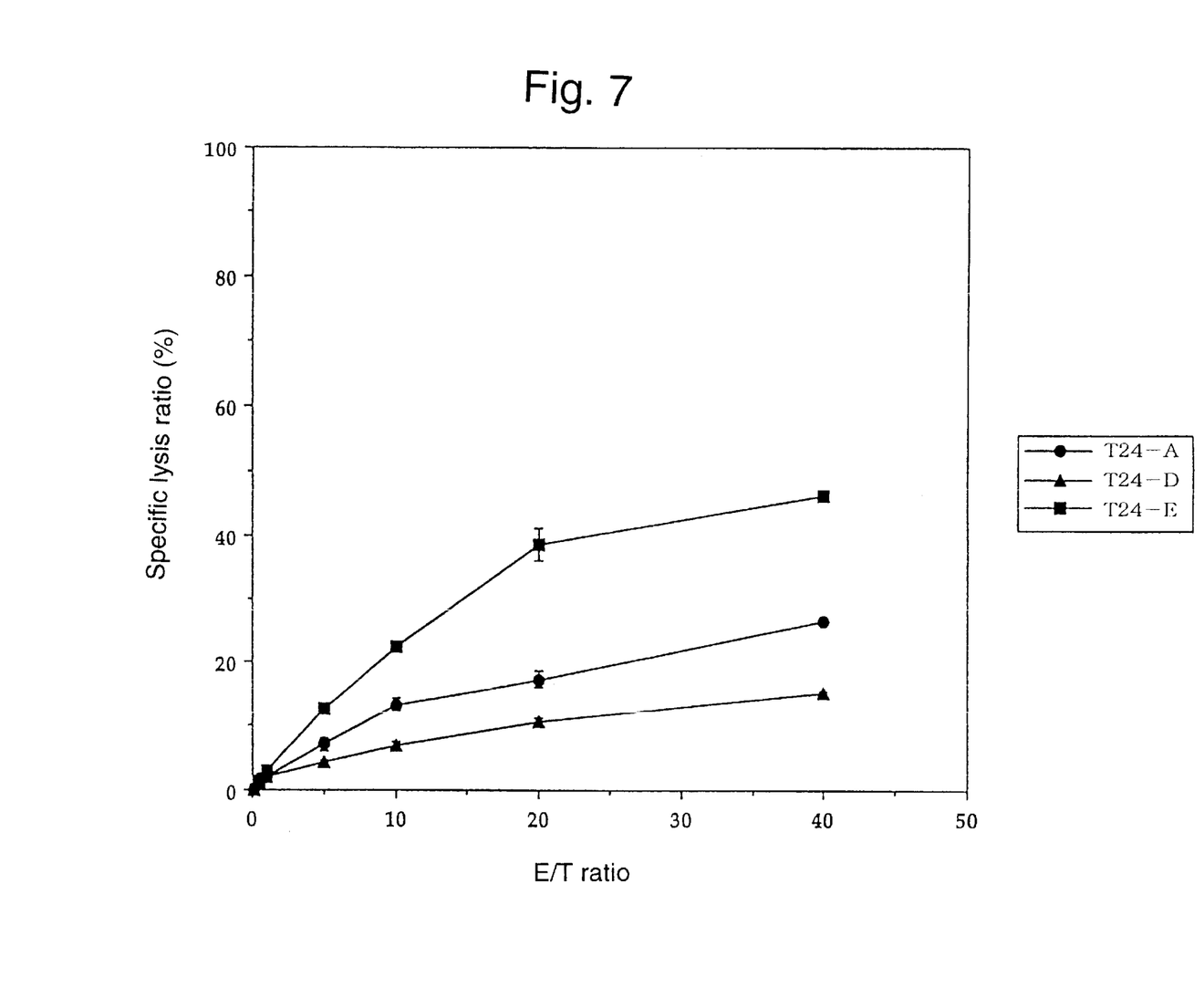
FIG. 7 is a graph showing a relation of a specific lysis ratio relative to an E/T ratio when Vγ2Vδ2 type T cells treated in Test example 6, subsequently frozen for preservation and thawed, acted on T 24 cells.

Using the sodium salt of 2-methyl-3-butenyl-1-pyrophosphoric acid obtained in Example, proliferation of the human Vγ2Vδ2 type T cells by treatment of the human peripheral blood and induction and enhancement as well as preservation by freezing and thawing were conducted in the same manner as in Test example 4. The treated and preserved blood was acted on the T24 cells to analyze cytotoxicity. The results are shown in FIG. 7. In FIG. 7, the transverse axis shows an E/T ratio, and the vertical axis shows a specific lysis ratio.

As is apparent from FIG. 7, cytotoxicity reached approximately a plateau when the E/T ratio is 20:1 in any case while there is a difference in degree. And it is observed that the antitumor effect was maintained even after the cells were preserved by freezing.

TEST EXAMPLE 7

Figure 8:
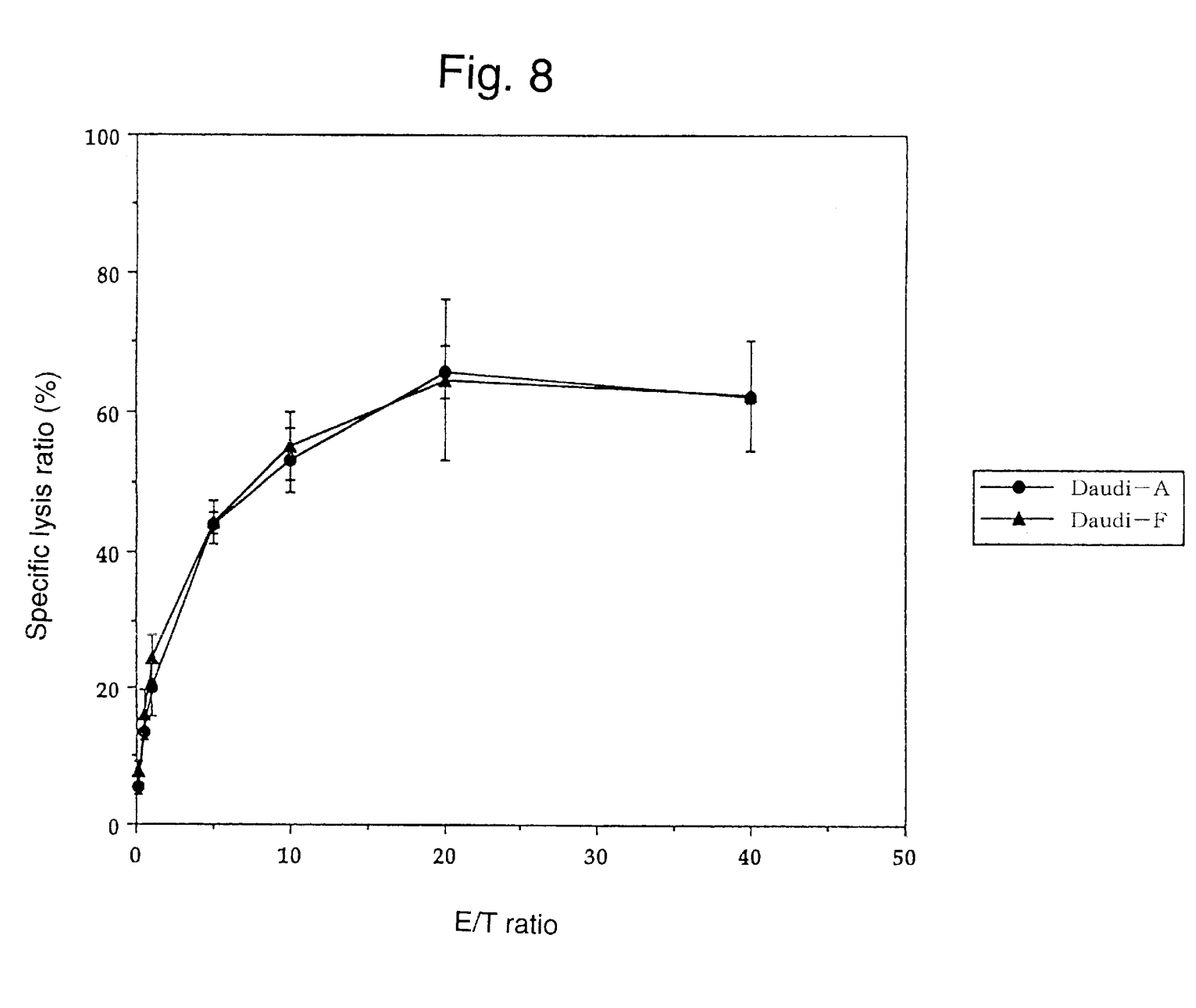
FIG. 8 is a graph showing a relation of a specific lysis ratio relative to an E/T ratio when each of the Vγ2Vδ2 type T cells collected from the peripheral blood of A, treated, frozen for preservation and thawed and Vγ2Vδ2 type T cells collected from the peripheral blood of F and treated respectively acted on Daudi cells.
Figure 9:
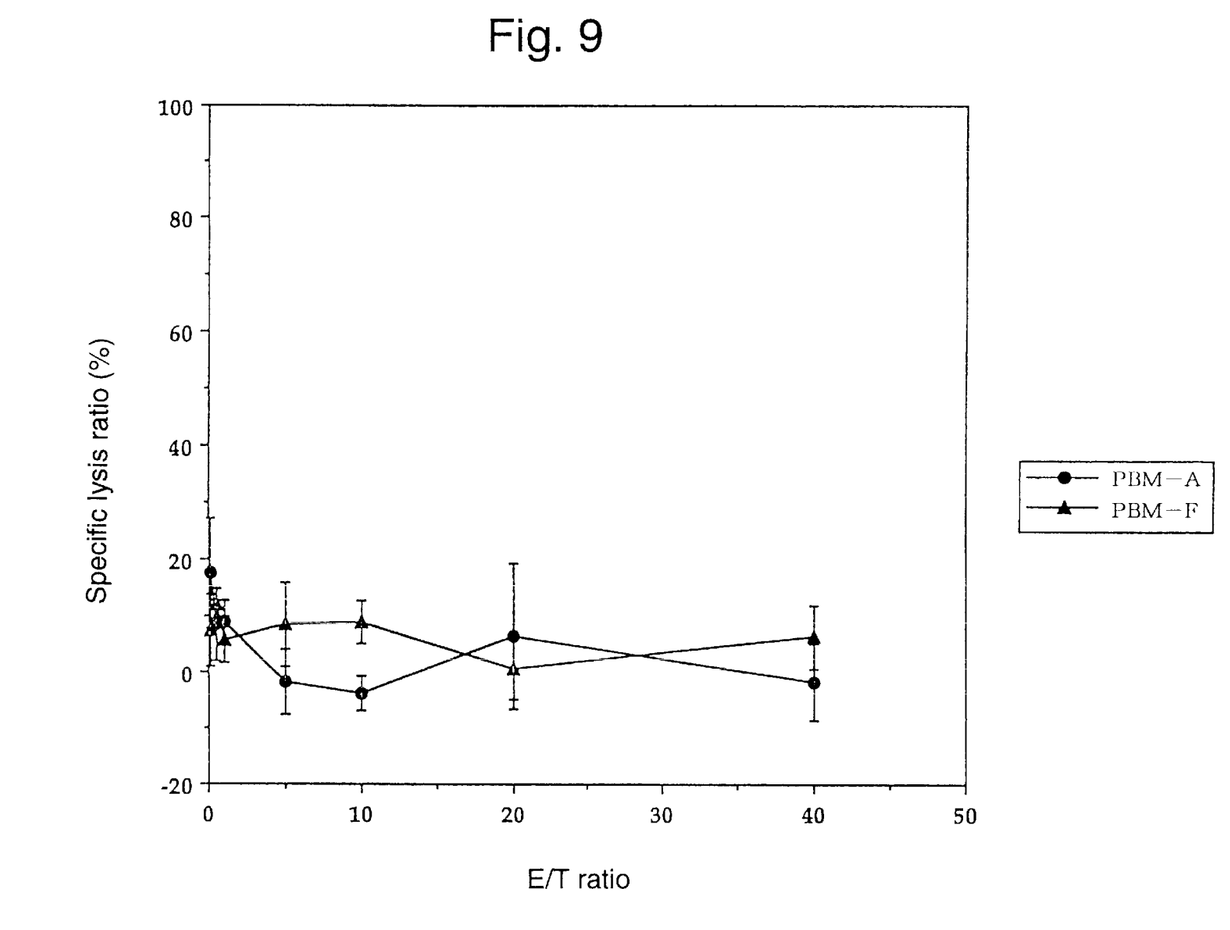
FIG. 9 is a graph showing a relation of a specific lysis ratio relative to an E/T ratio when each of the Vγ2Vδ2 type T cells collected from the peripheral blood of A, treated, frozen for preservation and thawed and Vγ2Vδ2 type T cells collected from the peripheral blood of F and treated respectively acted on normal peripheral blood cells of A.

Using the sodium salt of 2-methyl-3-butenyl-1-pyrophosphoric acid obtained in Test example and using the peripheral blood of the volunteer A, proliferation of the human Vγ2Vδ2 type T cells by treatment of the human peripheral blood and induction and enhancement were conducted according to the above-mentioned method. In the same manner as in Test example 4, the treated and preserved blood which had been preserved by freezing and thawed were acted on Daudi cells to analyze cytotoxicity. On the other hand, peripheral blood of other healthy volunteer F was treated according to the above-mentioned method and they were acted on Daudi cells in the same manner to analyze cytotoxicity. The results are shown in FIG. 8. Further, using the treated and preserved blood derived from A that had been preserved by freezing and thawed and the treated peripheral blood derived from F, cytotoxicity was analyzed based on the normal peripheral blood cells of A. The results are shown in FIG. 9. In those FIGS., the transverse axis shows an E/T ratio, and the vertical axis shows a specific lysis ratio.

As is apparent from FIG. 8, cytotoxicity reached approximately a plateau when E/T ratio is 20:1 in both cases of the peripheral bloods of A (after preservation by freezing and thawing) and F.

On the other hand, from the results for the peripheral bloods of A (after preservation by freezing and thawing) and F in FIG. 9, it is evident that the Vγ2Vδ2 type T cells whose antitumor activity was induced and potentiated by the sodium salt of 2-methyl-3-butenyl-1-pyrophosphoric acid do not attack the normal cells when they are used as they are or even after they are preserved by freezing and thawed.

TEST EXAMPLE 8

10 ml of the peripheral blood collected from a healthy volunteer G was subjected to Ficoll-Paque specific gravity centrifugation to purify the peripheral blood mononuclear cells and they were suspended in a Yssel's medium. The cells were apportioned into a 24-hole plate so that the number of the cells becomes a concentration of 2.5 million/1.5 ml/hole, and then, according to the above-mentioned method, treatments 1 to 5 were conducted as shown in Table 1. Among them, treatment 1 is a treatment using only a culture medium and treatment 2 solely uses interleukin-2, and both treatments are for comparison. Treatments 3 to 5 are treatments of the present invention using the sodium salt of 2-methyl-3-butenyl-1-pyrophosphoric acid obtained in Example and interleukin-2 in combination. On the day 11 after conducting the treatment, a ratio of Vγ2Vδ2 type T cells in existing CD3 cells was calculated. The results are shown in Table 1.

TABLE 1

| | Treatment | | |
|---|---|---|---|
| Treatment No. | Sodium salt of 2-methyl-3-butenyl-1-pyrophosphoric acid [μM] | Interleukin-2 [U/ml] | $V_\gamma V\delta 2$ type T cells/CD3 cells [%] |
| 1* | — | — | 6.7 |
| 2* | — | 10 | 6.9 |
| 3 | 2 | 10 | 58.3 |
| 4 | 20 | 10 | 85.5 |
| 5 | 200 | 10 | 94.5 |

*: Comparative treatment

As is apparent from Table 1, when interleukin-2 was used solely, the ratio of Vγ2Vδ2 type T cells was approximately the same level as that of the treatment using only the culture medium. On the contrary, in the treatments 3 to 5 of the present invention, proliferation of the Vγ2Vδ2 type T cells by the sodium salt of 2-methyl-3-butenyl-1-pyrophosphoric acid was significant and the ratios were increased accompanying an increase of the amount of the pyrophosphoric acid compound added.

Industrial Applicability

As is explained above, 2-methyl-3-butenyl-1-pyrophosphoric acid, a pharmaceutically acceptable salt thereof, especially the sodium salt of 2-methyl-3-butenyl-1-pyrophosphoric acid of the present invention and/or an agent for treating lymphocytes containing a hydrate thereof as an active component stimulate and proliferate the human Vγ2Vδ2 type T cells, and at the same time, exhibit a specific effect to induce and enhance the antitumor effect thereof. In addition, they do not exhibit any cytotoxicity on the self cells. They can specifically activate a natural killer cell such as the human Vγ2Vδ2 type T cell with a low antigen concentration.

The agent for treating lymphocytes of the present invention can be applied to various clinical fields. For example, peripheral blood of a cancer patient or a healthy person is collected and treated by the agent for treating lymphocytes of the present invention to stimulate Vγ2Vδ2 type T cells, thereby proliferating them polyclonally as well as inducing and enhancing the antitumor activity thereof. By re-circulating those lymphocytes in the body, the antitumor activity in vivo can be expected. In that case, it is possible to preserve the lymphocytes by freezing, they can be frozen and preserved at a suitable stage, and can be administered to the patient as a need arises.

What is claimed is:

1. A pharmaceutically acceptable salt of 2-methyl-3-butenyl-1-pyrophosphoric acid.

2. A sodium salt of 2-methyl-3-butenyl-1-pyrophosphoric acid represented by the formula (I):

wherein each of X independently represents a hydrogen atom or a sodium atom, at least one of which is a sodium atom.

3. The sodium salt according to claim 2, wherein two of X are sodium atoms.

4. An agent for treating lymphocytes which comprises at least one of 2-methyl-3-butenyl-1-pyrophosphoric acid, a pharmaceutically acceptable salt thereof, on a hydrate thereof.

5. The agent for treating lymphocytes according to claim 4, wherein the pharmaceutically acceptable salt of 2-methyl-3-butenyl-1-pyrophosphoric acid is a sodium salt of 2-methyl-3-butenyl-1-pyrophosphoric acid.

6. The agent for treating lymphocytes according to claim 4, wherein the agent further comprises interleukin-2.

7. The agent for treating lymphocytes according to claim 5, wherein the agent further comprises interleukin-2.

* * * * *